US00PP10662P

United States Patent [19]

VandenBerg

[11] Patent Number: Plant 10,662

[45] Date of Patent: Oct. 27, 1998

[54] CHRYSANTHEMUM PLANT NAMED 'YELLOW TRAVIATA'

[75] Inventor: Cornelis P. VandenBerg, Salinas, Calif.

[73] Assignee: Yoder Brothers, Inc., Barberton, Ohio

[21] Appl. No.: 786,420

[22] Filed: Jan. 21, 1997

[51] Int. Cl.[6] ..... A01H 5/00

[52] U.S. Cl. ..... Plt./78

[58] Field of Search ..... Plt./78, 82.2

[56] References Cited

U.S. PATENT DOCUMENTS 4,616,099 10/1986 Sparkes ..... 47/58

OTHER PUBLICATIONS

Broertjes, et al., "A mutant of a mutant of a . . . Irradiation of progressive radiation–induced mutants in a mutation breeding programme with *Chrysanthemum morifolium*", Euphytica 29:525–530.

Gosling, ed., 1979, "The Chrysanthemum Manual–6$^{th}$ edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x–rays", Am. Soc. Hart. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X– and gamma radiation", Euphytica 15:204–210.

UPOV–ROM, 1997/04, Plant Variety Database, GTI Jouve Retrieval Software, citation for 'Yellow Traviata'.

*Primary Examiner*—Howard J. Locker
*Attorney, Agent, or Firm*—Foley & Lardner

[57] ABSTRACT

A Chrysanthemum plant named Yellow Traviata particularly characterized by its flat capitulum form; quilled-decorative capitulum type; yellow ray floret color diameter across face of capitulum of 92 to 99 mm when fully opened, when grown as a single stem spray cut mum; when grown as a single stem disbudded cut mum the diameter of capitulum is 132 to 145 mm; flowering response in Salinas under normal temperatures is 56 to 61 days after start of short days. Flowering response in Bogotá, Colombia is 67 to 77 days after start of short days; plant height is 84 to 102 cm when grown in Salinas with 18 long days prior to start of short days; height is 86 to 97 cm when grown in Bogotá with 21 long days prior to start of short days; peduncle length of the first and the fourth lateral at flowering after removing the apical bud without growth regulator applications is 8 to 10 cm and 13 to 15 cm when grown in Salinas, Calif. and in Bogotá, Colombia; recommended both as a disbudded and a spray cut mum; and uniform flowering in year round flowerings in both Salinas, Calif. and in Bogotá, Colombia.

1 Drawing Sheet

The present invention comprises a new and distinct cultivar of Chrysanthemum, botanically known as *Dendranthema grandiflora*, and referred to by the cultivar name Yellow Traviata.

Yellow Traviata, identified as 0229 (91-L24C04), is a product of a mutation induction program. The new cultivar was discovered and selected by inventor Cornelis P. VandenBerg on Jun. 21, 1994 in a controlled environment in Salinas, Calif. as one flowering plant within a flowering block established as rooted cuttings from stock plants which had been exposed as unrooted cuttings to an X-ray source of 2000 rads in Fort Myers, Fla. on Nov. 18, 1993. The irradiated parent cultivar was the cultivar Traviata, disclosed in U.S. Plant Patent application, Ser. No. 08/702,295 and described as a flat decorative spray cut mum with a quilled-decorative capitulum type and a white ray floret color. Traviata was first introduced in the United States and Canada in July 1996.

The irradiation program resulting in Yellow Traviata had as its primary objective the expansion of color ranges of the parent cultivar Traviata. The irradiation program comprised irradiation of cuttings of the parent cultivar at irradiation levels of 1500, 1750 and 2000 rads. A total of 543 cuttings harvested from a total of 225 irradiated plants were planted on Apr. 4, 1994. Of these, 3 initial selections were made, which selections were then revegetated and reflowered. Three consecutive flowerings resulted in maintaining all three selections as PIs (Possible Introductions), which were further trialed in Salinas, Calif. and in Bogotá, Colombia, ultimately resulting in the decision to introduce one selection as Yellow Traviata. One remaining selection is still maintained and trialed and the other selection has been discarded.

The first act of asexual reproduction of Yellow Traviata was accomplished when vegetative cuttings were taken from the initial selection in August of 1994 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Traviata are firmly fixed and are retained through successive generations of asexual reproduction.

Yellow Traviata has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogotá, Colombia, under greenhouse conditions which approximate those generally used in commercial greenhouse practice. The low night temperature tolerance was determined in repeated flowerings in Bogotá, Colombia, with an average minimum low night temperature inside the greenhouse during our trials ranging as low as 5 to 8 degrees Celsius. The following traits have been repeatedly observed and are determined to be basic characteristics of Yellow Traviata, which, in combination, distinguish this Chrysanthemum as a new and distinct cultivar:

1. Flat capitulum form.
2. Quilled-decorative capitulum type.
3. Yellow ray floret color.
4. Diameter across face of capitulum of 92 to 99 mm when fully opened, when grown as a single stem spray cut mum; when grown as a single stem disbudded cut mum the diameter of capitulum is 132 to 145 mm.
5. Flowering response in Salinas under normal temperatures is 56 to 61 days after start of short days. Flowering response in Bogotá, Colombia is 67 to 77 days after start of short days.
6. Plant height is 84 to 102 cm when grown in Salinas with 18 long days prior to start of short days; height is 86 to 97 cm when grown in Bogotá with 21 long days prior to start of short days.
7. Peduncle length of the first and the fourth lateral at flowering after removing the apical bud without growth regulator applications is 8 to 10 cm and 13 to 15 cm when grown in Salinas, Calif. and in Bogotá, Colombia.
8. Recommended both as a disbudded and a spray cut mum.
9. Uniform flowering in year round flowerings in both Salinas, Calif. and in Bogotá, Colombia.

Excellent low night temperature tolerance, flowering in Bogota, Colombia at average minimum low night temperatures inside the greenhouse as low as 5° to 8° Celsius.

The accompanying photographic drawing is a side view of a single stem cut spray mum of Yellow Traviata, with the colors being as nearly true as possible with illustrations of this type.

Of the commercial cultivars known to the inventor, the most similar in comparison to Yellow Traviata is the parent cultivar Traviata. All traits of Yellow Traviata are similar to those of Traviata, except for the ray floret color, the diameter of capitulum, the ray floret shape and the flowering response to short days. The flowering response for 'Yellow Traviata' in Salinas is 56–61 days after start of short days and the flowering response in Bogotá is 67 to 77 days after start of short days. In comparison, the flowering response for 'Traviata' in Salinas is 53–58 after days after start of short days and the flowering response in Bogotá is 65–74 days after start of short days. The ray floret color of Yellow Traviata is yellow (R.H.S. 5B to 5C), while the ray floret color of Traviata is described as white (R.H.S. 155D). Yellow Traviata has a slightly larger diameter of capitulum, thicker ray floret quills and a larger, more rounded ray floret tip when compared with Traviata.

In the following description color references are made to The Royal Horticultural Society Colour Chart. The color values were determined on plant material grown as a single stem spray cut mum grown in Salinas, Calif. on Jun. 13, 1996.

Classification:

*Botanical.*—*Dendranthema grandiflora* cv Yellow Traviata.

*Commercial.*—Flat quilled-decorative spray and disbud cut mum.

Inflorescence

A. Capitulum:

*Form.*—Flat.

*Type.*—Quilled-decorative.

*Diameter across face.*—92 to 99 mm as spray, 132 to 145 mm as disbud when fully opened.

B. Corolla of ray florets:

*Color* (*general tonality from a distance of three meters*).—Yellow.

*Color* (*upper surface*).—5B to 5C.

*Color* (*under surface*).—5B to 5C.

*Shape.*—Straight, quilled with slight spoon at the ray floret tip.

C. Corolla of disc florets:

*Color* (*mature*).—Closest to 14A.

*Color* (*immature*).—Closest to 144A.

D. Reproductive organs:

*Androecium.*—Present on disc florets only; no pollen.

*Gynoecium.*—Present on both ray and disc florets.

Plant

A. General appearance:

*Height.*—84 to 102 cm when grown in Salinas with 18 long days prior to start of short days; height is 86 to 97 cm when grown in Bogotá with 21 long days prior to start of short days.

B. Foliage:

*Color* (*upper surface*).—147A.

*Color* (*under surface*).—147B.

*Shape.*—Long, narrow, lobed and serrated.

What is claimed is:

1. A new and distinct Chrysanthemum plant named Yellow Traviata, as described and illustrated.

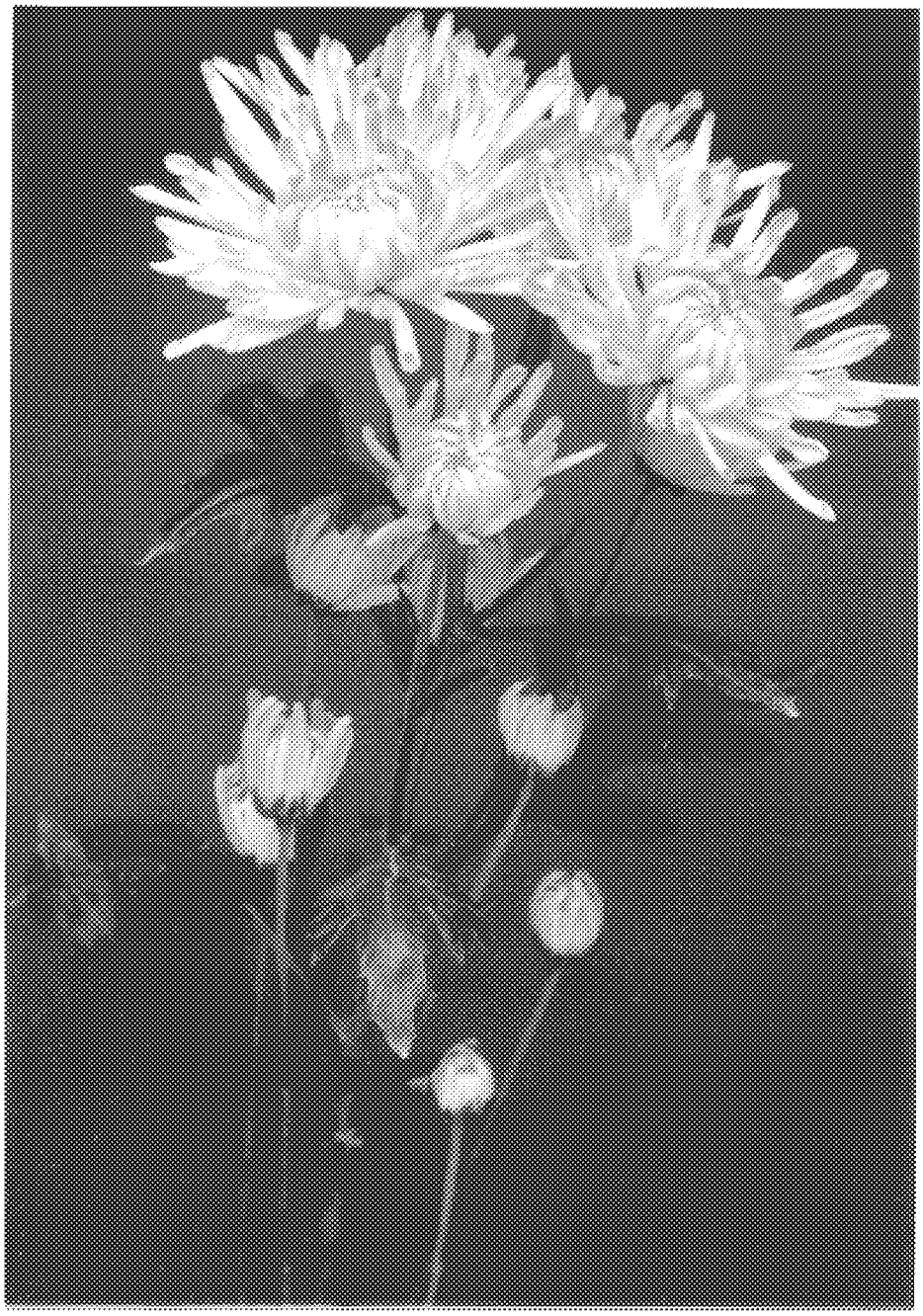

* * * * *